(12) United States Patent
Alexandrov et al.

(10) Patent No.: US 7,335,760 B2
(45) Date of Patent: Feb. 26, 2008

(54) NUCLEIC ACID SEQUENCES ENCODING ZINC FINGER PROTEINS

(75) Inventors: Nickolai Alexandrov, Thousand Oaks, CA (US); Vyacheslav Brover, Simi Valley, CA (US); Kenneth Feldmann, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/396,378

(22) Filed: Mar. 31, 2006

(65) Prior Publication Data

US 2006/0235213 A1 Oct. 19, 2006

Related U.S. Application Data

(63) Continuation-in-part of application No. 11/241,607, filed on Sep. 30, 2005.

(60) Provisional application No. 60/638,820, filed on Dec. 22, 2004.

(51) Int. Cl.
C12N 15/29 (2006.01)
(52) U.S. Cl. .................................................. 536/23.6
(58) Field of Classification Search .................... None
See application file for complete search history.

(56) References Cited

U.S. PATENT DOCUMENTS

| | | | |
|---|---|---|---|
| 4,987,071 A | 1/1991 | Cech et al. ............. 435/91.31 |
| 5,034,323 A | 7/1991 | Jorgensen et al. .......... 807/282 |
| 5,204,253 A | 4/1993 | Sanford et al. ............. 435/459 |
| 5,231,020 A | 7/1993 | Jorgensen et al. .......... 800/281 |
| 5,254,678 A | 10/1993 | Haseloff et al. ............ 536/23.2 |
| 5,538,880 A | 7/1996 | Lundquist et al. .......... 800/265 |
| 5,766,847 A | 6/1998 | Jackle et al. .................. 435/6 |
| 5,878,215 A | 3/1999 | Kling et al. ................ 709/207 |
| 5,945,306 A | 8/1999 | Bandman et al. .......... 435/69.1 |
| 5,998,700 A | 12/1999 | Lightfoot et al. ........... 800/278 |
| 6,004,753 A | 12/1999 | Yue et al. ....................... 435/6 |
| 6,013,863 A | 1/2000 | Lundquist et al. .......... 800/293 |
| 6,287,778 B1 | 9/2001 | Huang et al. .................... 435/6 |
| 6,326,527 B1 | 12/2001 | Kirihara et al. ............ 800/278 |
| 6,329,571 B1 | 12/2001 | Hiei ............................ 800/294 |
| 6,423,885 B1 | 7/2002 | Waterhouse et al. ........ 800/278 |
| 6,452,067 B1 | 9/2002 | Bedbrook et al. .......... 800/278 |
| 6,500,614 B1 | 12/2002 | Arguello et al. ................ 435/6 |
| 6,573,099 B2 | 6/2003 | Graham ...................... 435/455 |
| 6,777,588 B2 | 8/2004 | Waterhouse et al. ........ 800/280 |
| 6,906,244 B2 | 6/2005 | Fischer et al. ............. 800/298 |
| 2003/0180945 A1 | 9/2003 | Wang et al. .................. 435/375 |
| 2003/0233670 A1 | 12/2003 | Edgerton et al. ........... 800/278 |
| 2004/0137466 A1 | 7/2004 | Jofuku et al. ................... 435/6 |
| 2004/0214330 A1 | 10/2004 | Waterhouse et al. ........ 435/455 |
| 2006/0041952 A1 | 2/2006 | Cook ........................... 800/278 |

FOREIGN PATENT DOCUMENTS

| | | |
|---|---|---|
| EP | 292 435 | 11/1988 |
| EP | 0 465 875 | 1/1992 |
| EP | 0 513 849 | 11/1992 |
| EP | 0534858 | 3/1993 |
| EP | A 0 511 979 | 8/1994 |
| JP | 2004 121047 | 4/2004 |
| WO | 95/06128 | 3/1995 |
| WO | 96/21737 | 7/1996 |
| WO | 98/36083 | 8/1998 |
| WO | 98/53083 | 11/1998 |
| WO | 99/032619 | 7/1999 |
| WO | 99/53050 | 10/1999 |
| WO | 00/31281 | 6/2000 |
| WO | 01/18191 | 3/2001 |
| WO | 01/035725 | 5/2001 |
| WO | 01/75164 | 10/2001 |
| WO | 02/010210 | 2/2002 |
| WO | 02/015675 | 2/2002 |
| WO | 02/016655 | 2/2002 |
| WO | 02/046449 | 6/2002 |
| WO | 02/181714 | 10/2002 |
| WO | 03/013227 | 2/2003 |
| WO | 03/095654 | 11/2003 |

OTHER PUBLICATIONS

GenBank No. U93215, dated Feb. 27, 2002.
GenBank No. AF129516, dated Apr. 6, 1999.
GenBank No. AF096096, dated Jan. 25, 1999.
GenBank No. L05934, dated Oct. 22, 1993.
GenBank No. AL163815.1 dated Nov. 14, 2006.
GenBank No. Q9LPV5, dated Mar. 1, 2004.
GenBank No. CAB87717, dated Nov. 14, 2006.
Abler, "Isolation and characterization of a genomic sequence encoding the maize *Cat3* catalase gene" *Plant Mol. Biol.*, 22:1031-1038 (1993).
Ahn et al., "Homoeologous relationship of rice, wheat and maize chromosomes" *Molecular and General Genetics*, 241:483-90 (1993).
Alonso-Blanco et al. (Methods in Molecular Biology, vol. 82, "*Arabidopsis* Protocols", pp. 137-146, J.M. Martinez-Zapater and J. Salinas, eds., c. 1998 by *Humana Press*, Totowa, NJ).
An et al. "New cloning vehicles for transformation of higher plants" *The EMBO Journal*, 4(2):277-284 (1985).
Apuya et al. "RASPBERRY3 Gene Encodes a Novel Protein Important for Embryo Development," *Plant Physiology*, 129(2):691-705 (2002).
Armaleo et al. "Biolistic nuclear transformation of *Saccharomyces cerevisiae* and other fungi" (1990) *Current Genetics*, 17:97-103.
Baerson et al., "Developmental regulation of an acyl carrier protein gene promoter in vegetative and reproductive tissues" *Plant Mol Biol.*, 22(2):255-267 (1993).
Bateman et al., "Pfam 3.1: 1313 multiple alignments and profile HMMs match the majority of proteins" *Nucl. Acids Res.* 27:260-262 (1999).

(Continued)

*Primary Examiner*—James Martinell
(74) *Attorney, Agent, or Firm*—Fish & Richardson P.C.

(57) ABSTRACT

Isolated polynucleotides and polypeptides encoded thereby are described, together with the use of those products for making transgenic plants.

1 Claim, No Drawings

OTHER PUBLICATIONS

Baud, S.; Boutin, J.-P.; Miquel, M.; Lepiniec, L.; Rochat, C. An integrated overview of seed development in *Arabidopsis thaliana* ecotype WS, *Plant Physiol. Biochem.* 40 (2002) 151-160.

Bechtold et al., "*In planta* Agrobacterium mediated gene transfer by infiltration of adult *Arabidopsis thaliana* plants" *C.R. Acad. Sci. Paris*, 316:1194-1199 (1993).

Bonner et al., "Reduction in the Rate of DNA reassociation by Sequence Divergence" *J. Mol. Biol.*, 81:123 (1973).

Bradshaw et al., "A new vector for recombination-based cloning of large DNA fragments from yeast artificial chromosomes" *Nucl. Acids. Res.*, 23:4850-4856 (1995).

Broothaerts et al. "Gene Transfer to Plants by Diverse Species of Bacteria," *Nature*, vol. 433, pp. 629-633 (2005).

Brummell, et al. "Inverted repeat of a heterologous 3'-untranslated region for high-effeiciency, high-throughput gene silencing" (2003) *Plant J,*. 33:793-800.

Burke et al., "Cloning of large segments of exogenous DNA into yeast by means of artificial chromosome vectors" *Science*, 236:806-812 (1987).

Burr et al ("Mapping Genes with Recombinant Inbreds", pp. 249-254. In Freeling, M. and V. Walbot (Ed.), The Maize Handbook, c. 1994 by Springer-Verlag New York, Inc.: New York, NY, USA; Berlin Germany.

Burr et al., "Gene mapping with recombinant inbreds in maize" *Genetics*, 118:519 (1998).

Bustos, et al., "Regulation of B-Glucuronidase Expression in Transgenic Tobacco Plants by an A/T-Rich, cis-Acting Sequence Found Upstream of a French Bean—Phaseolin Gene" *Plant Cell*, 1:839-854 (1989).

Carels et al., "Compositional properties of homologous coding sequences from plants", *J. Mol. Evol.*, 46:45 (1998).

Cerdan et al., "A 146 bp fragment of the tobacco Lhcb1*2 promoter confers very-low-influence, low-fluence and high-irradiance responses of phytochrome to a minimal CaMV 35S promoter" *Plant Mol. Biol.* 33:245-255 (1997).

Chan et al. "*Agrobacterium*-mediated production of transgenic rice plants expressing a chimeric a-amylase promoter/β-glucuronidase gene" Plant Mol. Biol. 22: 491-506 (1993).

Chen et al., "Functional analysis of regulatory elements in a plant embryo-specific gene" *Proc Natl Acad Sci USA*, 83:8560-8564 (1986).

Chenna, et al. "Multiple sequence alignment with the Clustal series of programs" *Nucleic Acids Res.*, 31 (13):3497-500 (2003).

Chichkova et al., "Transgenic tobacco plants that overexpress alfalfa NADH-glutamate synthase have higher carbon and nitrogen content" *Journal of Experimental Botany*, 52(364):2079-2087 (2001).

Christou, "Strategies for variety-independent genetic transformation of important cereals, legumes and woody species utilizing particle bombardment" *Euphytica*, 85(1-3):13-27, (1995).

Conceicao et al., "a cotyledon region is responsible for the different spatial expression patterns of *Arabidopsis* 2S albumin genes" *The Plant Journal*, 5:493-505 (1994).

Conkling et al., "Isolation of transcriptionally regulated root-specific genes from tobacco" *Plant Physiol.*, 93:1203-1211 (1990).

Conner and Domisse "Monocotyledonous plants as hosts for *Agrobacterium*" *Int. J. Plant Sci.* 153:550-555 (1992).

de Feyter et al., "Expressing Ribozymes in Plants," *Methods in Molecular Biology*, vol. 74, Chapter 43:403-415.

deVicente and Tanksley "QTL analaysis of transgressive segregation in an interspecific tomato cross" *Genetics*, 134:585 (1993).

Dietrich et al., "AtPTR1, a plasma membrane peptide transporter expressed during seed germination and in vascular tissue of *Arabidopsis*" *Plant Journal*, 40(4):488-499 (2004).

Escudero et al. "T-DNA transfer in meristematic cells of maize provided with intracellular *Agrobacterium*" *Plant J.* 10:355 (1996).

Evans et al., Protoplasts Isolation and Culture in "Handbook of Plant Cell Culture," pp. 124-176, *MacMillan Publishing Company*, New York, 1983.

Ezeagu, I.E.; Petzke, J.K.; Metges, C.C.; Akinsoyinu, A.O.; Ologhobo, A.D. Seed protein contents and nitrogen-to-protein conversion factors for some uncultivated tropical plant seeds, *Food Chemistry*, 78 (2002) 105-109.

Fejes et al., "A 268 bp upstream sequence mediates the circadian clock-regulated transcription of the wheat Cab-1 gene in transgenic plants" *Plant Mol. Biol.*, 15:921-932 (1990).

Fennoy et al. "Synonymous codon usage in *Zea mays* L. nuclear genes is varied by levels of C and G-ending codons" *Nucleic Acids Research*, 21(23):5294 (1993).

Foyer et al., "Adaptations of photosynthetic electron transport, carbon assimilation, and carbon partitioning in transgenic *Nicotiana plumbaginifolia* plants to changes in nitrate reductase activity" *Plant Physiology*, 104(1):171-178 (1994).

Fraisier et al., "Constitutive expression of putative high-affinity nitrate transporter in *Nicotiana plumbaginifolia*: evidence for post-transcriptional regulation by a reduced nitrogen source" *Plant Journal*, 23(4):489-496 (2000).

Fraley et al. "Genetic transformation in higher plants" *Crit. Rev. Plant. Sci.* 4, 1-46 (1986).

Frischauf et al., "Lambda replacement vectors carrying polylinker sequences" *J. Mol. Biol.*, 170:827-842 (1983).

Fromm et al. "Expression of genes transferred into monocot and dicot plant cells by electroporation" *Proc. Natl. Acad. Sci. USA*, 82:5824 (1985).

Fromm et al., "An octopine synthase enhancer directs tissue-specific expression and binds ASF-1, a factor from tobacco nuclear extracts" *The Plant Cell*, 1:977-984 (1989).

Fromm et al., "Inheritance and expression of chimeric genes in the progeny to transgenic maize plants" *Biotechnology*, (1990) 8:833-844.

Gardiner et al., "Development of a core FRLP map in maize using an immortalized $F_2$ population" *Genetics*, 134:917 (1993).

Biswas et al. "Transgenic indica rice (*Oryza sativa* L.) plants obtained by direct gene transfer to protoplats" *J. Biotechnol.*, 32:1-10 (1994).

Gleave, "A versatile binary vector system with a T-DNA organizational structure conductive to efficient integration of cloned DNA into the plant genome" *Plant Mol. Biol.*, 20:1203 (1992).

Gordon-Kamm et al. "Transformation of maize cells and regeneration of fertile transgenic plants" *Plant Cell*, (1990) 2:603-618.

Gould et al., "Transformation of *Zea mays* L. Using *Agrobacterium tummefaciens* and the shoot apex" *Plant Physiology*, 95:426 (1991).

Graves and Goldman, "The transformation of *Zea mays* seedling with *Agrobacterium tumefaciens*" *Plant Mol. Biol.*, 7:34 (1986).

Green, et al., "Binding site requirements for pea nuclear protein factor GT-1 correlate with sequences required for light-dependent transcriptional activation of the rbcS-3A gene" *EMBO J.* 7, 4035-4044 (1988).

Heath, J.D.; Weldon, R.; Monnot, C.; Meinke, D.W. Analysis of storage proteins in normal and aborted seeds from embryo-lethal mutants of *Arabidopsis thaliana*, *Planta* 169 (1986) 304-312.

Hamilton, "A binary-BAC system for plant transformation with high-molecular-weight DNA" *Gene*, 200:107-116 (1997).

Hamilton et al., "Stable transfer of intact high molecular weight DNA into plant chromosomes" *Proc. Natl. Acad. Sci. USA*, 93:9975-9979 (1996).

Herrera-Estrella et al., "Chimeric genes as dominant selectable markers in plant cells" *EMBO J.*, 2:987 (1983).

Hiei et al. "Efficient transformation of rice (*Oryza sativa L*) mediated by *Agrobacterium* and sequence analysis of the boundaries of the T-DNA" (1994) *Plant J.* 6:271-282.

Hong et al., "Promoter sequences from two different *Brassica napus* tapetal oleosin-like genes direct tapetal expression of B-glucuronidase in transgenic *Brassica* plants" *Plant Mol Biol.*, 34(3):549-555 (1997).

Hosoyama et al. "Oryzacystatin exogenously introduced into protoplasts and regeneration of transgenic rice" *Biosci. Biotechnol. Biochem.*, 58:1500 (1994).

Huang et al., "Cloning and functional characterization of an *Arabidopsis* nitrate transporter gene that encodes a constitutive component of low-affinity uptake" *Plant Cell*, 11(8):1381-1392 (1999).

Huynh et al., In: Glover NM (ed) DNA Cloning: A practical Approach, vol. 1 *Oxford: IRL Press* (1985) pp. 49-78.

Hwang et al., "Aleurone- and embryo-specific expression of the β-glucuronidase gene controlled by the barley *Chi26* and *Ltp1* promoters in transgenic rice" *Plant Cell Rep.*, (2001) 20:647-654.

Hyrup et al., "Peptide nucleic acids (PNA): Synthesis, properties and potential applications" *Bioorganic Med. Chem.*, 4: 5-23 (1996).

Ishida et al. "High efficiency transformation of maize (*Zea mays* L.) mediated by *Agrobacterium tumefaciens*" *Nature Biotechnology* (1996) 14:745.

Jordano, et al., "A sunflower helianthinin gene upstream sequence ensemble contains an enhancer and sites of nuclear protein interaction" *Plant Cell*, 1:855-866 (1989).

Keller and Manak (DNA Probes, 2nd Ed. pp. 1-25, c. 1993 by *Stockton Press*, New York, NY).

Klee et al. "*Agrobacterium*-mediated plant transformation and its further applications to plant biology" *Ann. Rev. of Plant Phys.*, 38:467 (1987).

Klein et al. "High-velocity microprojectiles for delivering nucleic acids into living cells" *Nature*, 327:70 (1987).

Koch et al., "Reduced amino acid content in transgenic potato tubers due to antisense inhibition of the leaf H+/amino acid symporter StAAP1" *Plant Journal*, 33(2):211-220 (2003).

Komari et al., "Vectors carrying two separate T-DNAs for co-transformation of higher plants mediated by *Agrobacterium tumefaciens* and segregation of transformants free from selection markers" *Plant J.*, 10:165 (1996).

Koziel et al. "Field performance of elite transgenic maize plants expressing an insecticidal protein derived from *Bacillus thuringiensis*" *Biotechnology* 11:194-200 (1993).

Lam et al., "Site-specific mutations alter in vitro factor binding and change promoter expression pattern in transgenic plants" *Proc. Natl. Acad. Sci. USA*, 86:7890-7894 (1989).

Li et al., "Oil content of arabidopsis seeds: The influence of seed anatomy, light and plant-to-plant variation" *Phytochemistry*, 2006, 67:904-915.

Luan et al., "A rice *cab* gene promoter contains separate *cis*-Acting elements that regulate expression in dicot and monocot plants" *Plant Cell*, 4:971-981 (1992).

Lubberstedt et al., "Promoters from genes for plastid proteins possess regions with different sensitivities toward red and blue light" *Plant Physiol.*, 104:997-1006 (1994).

Marra et al., "High throughput fingerprint analysis of large-insert clones" *Genomic Research*, 7:1072-1084 (1997).

Matsuoka et al., "Tissue-specific light-regulated expression directed by the promoter of a $C_4$ gene, maize pyruvate, orthophosphate dikinase, in a $C_3$ plant, rice" *Proc Natl Acad. Sci USA*, 90:9586-9590 (1993).

Matteucci et al. "Synthesis of Deoxyoligonucleotides on a polymer support" *J. Am. Chem. Soc.*, 103:3185 (1981).

May et al. "Generation of transgenic banana (*Musa acuminata*) plants via *Agrobacterium*-mediated transformation" (1995) *Bio/Technology* 13:486).

McClure et al., "Transcription, Organization, and Sequence of an Auxin-Regulated Gene Cluster in Soybean" *Plant Cell*, 1:229-239 (1989).

McCormac et al., "A flexible series of binary vectors for agrobacterium-mediated plant transformation" *Mol. Biotechnol.*, 8:199 (1997).

McCormick et al. "Leaf disc transformation of cultivated tomato (*L. esculentum*) using *Agrobacterium tumefaciens*" *Plant Cell Reports* 5, 81-84 (1986).

Meier, et al., "Elicitor-inducible and constitutive in Vivo DNA footprints indicate novel *cis*-acting elements in the promoter of a parsley gene encoding pathogenesis-related protein 1" *Plant Cell*, 3, 309-316 (1991).

Müller et al., "High meiotic stability of a foreign gene introduced into tobacco by *Agrobacterium*-mediated transformation" *Mol. Gen. Genet.*, 207:171 (1987).

Needleman and Wunsch "A general method applicable to the search for similarities in the amino acid sequence of two proteins" *J. Mol. Biol.*, 48:443 (1970).

Nehra et al. "Self-fertile transgenic wheat plants regenerated from isolated scutellar tissues following microprojectile bombardment with two distinct gene constructs" *Plant J.* 5, 285-297 (1994).

Panaud et al., "Frequency of microsatellite sequences in rice (*Oryza sative* L.)" *Genome*, 38:1170 (1995).

Paszkowski et al. "Direct gene transfer to plants" *EMBO J.*, 3:2717 (1984).

Pearson and Lipman "Improved tools for biological sequence comparison" *Proc. Natl. Acad. Sci. USA*, 85: 2444 (1988).

Perriman, et al., "Effective ribozyme delivery in plant cells" *Proc. Natl. Acad. Sci. USA*, 92(13):6175-6179 (1995).

Prioli and Söndahl "Plant regeneration and recovery of fertile plants from protoplasts of maize(*Zea mays* L.)" *Bio/Technology* 7, 589 (1989).

Refseth et al., "Hybridization capture of microsatellites directly from genomic DNA" *Electrophoresis*, 18:1519 (1997).

Rhee, K.C. "Determination of Total Nitrogen In Handbook of Food Analytical Chemistry—Water, Proteins, Enzymes, Lipids, and Carbohydrates. (R. Wrolstad, et al, ed.)" *John Wiley and Sons, Inc.*, 2005, pp. 105.

Riggs et al., "Cotyledon nuclear proteins bind to DNA fragments harboring regulatory elements of phytohemagglutinin genes" *The Plant Cell*, 1(6):609-621 (1989).

Ritala et al. "Fertile transgenic barley by particle bombardment of immature embryos" *Plant Mol. Biol.* 24:317-325 (1994).

Ritchie et al. "*Agrobacterium tumefaciens*-mediated expression of gusA in maize tissues" *Transgenic Res.* 2:252-265 (1993).

Rivera et al., "Genomic evidence for two functionally distinct gene classes" *Proc. Natl. Acad. Sci. USA*, 95:6239-6244 (1998).

Salomon et al., "Genetic identification of functions of TR-DNA transcripts in octopine crown galls" *EMBO J.*, 3:141 (1984).

Sambrook et al. (Molecular Cloning, a Laboratory Manual, 2nd ed., c. 1989 by *Cold Spring Harbor Laboratory Press*, Cold Spring Harbor, NY). pp. 9.34-9.55.

Senior et al., "Simple sequence repeat markers developed from Maize sequences found in the Genbank database: Map construction" *Crop Science*, 36:1676 (1996).

Sheridan et al., "the *mac1* gene: Controlling the commitment to the meiotic pathway in maize" *Genetics*, 142:1009-1020 (1996).

Shillito et al. "Regeneration of fertile plants from protoplasts of elite inbred maize" *Bio/Technology* 7:581 (1989).

Shizuya et al., "Cloning and stable maintenance of 300-kilobase-pair fragments of human DNA in *Escherichia coli* using an F-factor-based vector" *Proc. Natl. Acad. Sci. USA*, 89:8794-8797 (1992).

Slocombe et al., "Temporal and tissue-specific regulation of a *Brassica napus* steroyl-acyl carrier protein desaturase gene" *Plant Physiol*, 104(4):167-176 (1994).

Smith and Waterman, "Comparison of Biosequences" *Advances in Applied Mathematics.*, 2:482 (1981).

Sonnhammer et al., "Pfam: multiple sequence alignments and HMM-profiles of protein domains" *Nucl. Acids Res.*, 26: 320-322 (1998).

Sonnhammer et al., "Pfam: A comprehensive database of protein domain families based on seed alignments", *Proteins*, 28:405-420 (1997).

Spencer et al. "Bialaphos selection of stable transformants from maize cell culture" *Theor. Appl. Genet.*, 79:625-631 (1990).

Sternberg et al., "Bacteriophage P1 cloning system for the isolation, amplification, and recovery of DNA fragments as large as 100 kilobase pairs" *Proc. Natl. Acad. Sci. USA*, 87(1):103-7 (1990).

Summerton and Weller, "Morpholino antisense oligomers: Design, preparation, and properties", *Antisense Nucleic Acid Drug Dev.*, 7:187-195 (1997).

Tanksley and McCouch, "Seed banks and molecular maps: Unlocking genetic potential from the wild" *Science*, 277:1063 (1997).

Taramino et al., "Simple sequence repeats for germplasm analysis and mapping in maize" *Genome*, 39:277 (1996).

Tijessen, "Hybridization with Nucleic Acid Probes" in Laboratory Techniques in Biochemistry and Molecular Biology, P.C. vand der Vliet, ed., c. 1993 by *Elsevier*, Amsterdam, pp. 19-78.

Truernit et al., "The promoter of the *Arabidopsis thaliana* SUC2 sucrose-H+ symporter gene directs expression of B-glucuronidase to the phloem: evidence for phloem loading and unloading by SUC3" *Planta*, 196:564-570 (1995).

Tuskan et al., "The genome of black cottonwood, *Populus trichocarpa*" *Science*, 2006, 313(5793):1596-604.

Urao et al., "Molecular cloning and characterization of a gene that encodes a MYC-related protein in *Arabidopsis*" *Plant Mol. Biol.*, 32:571-57 (1996).

Urdea et al. "Chemical synthesis of a gene for human epidermal growth factor urogastrone and its expression in yeast" *Proc. Natl. Acad. Sci. USA*, 80:7461 (1983).

Vasil et al. "Rapid production of transgenic wheat plants by direct bombardment of cultured immature embryos" (1993) *Bio/Technology* 11:1553-1558.

Venkateswarlu et al., "Evidence for T-DNA mediated gene targeting to tobacco chloroplasts" *Biotechnology*, 9:1103 (1991).

Walden et al., "A novel 205-kilodalton testis-specific serine/threonine protein kinase associated with microtubules of the spermatid manchette" *Mol. Cell. Biol.*, 13:7625-7635 (1990).

Wan and Lemaux "Generation of large number of independently transformed fertile barley plants" (1994) *Plant Physiol.*, 104:37-48.

Weber et al., "Interaction of cytosolic and plastidic nitrogen metabolism in plants" *Journal of Experimental Botany*, 53(370):865-874 (2002).

Weising et al., "Foreign genes in plants: transfer, structure, expression, and applications" *Ann. Rev. Genet.*, 22:421 (1988).

Willmitzer (Willmitzer, L. (1993) Transgenic plants. In: Biotechnology, A Multi-Volume Comprehensive Treatise (H.J. Rehm, G. Reed, A. Püler, P. Stadler, eds.), vol. 2, 627-659, VCH Weinheim-New York-Basel-Cambridge).

Wilmink et al. "Expression of the GUS-gene in the monocot tulip after introduction by particle bombardment and *Agrobacterium*" *Plant Cell Reports* 11:76-80 (1992).

Yamamoto et al., "The promoter of a pine photosynthetic gene allows expression of a B-glucuronidase reporter gene in transgenic rice plants in a light-independent but tissue-specific manner" *Plant Cell Physiol.* 35:773-778 (1994).

Yanagisawa et al., "Metabolic engineering with Dof1 transcription factor in plants: Improved nitrogen assimilation and growth under low-nitrogen conditions" *PNAS*, 101(20):7833-7838 (2004).

Zhang, et al., "DNA sequences that activate isocitrate lyase gene expression during late embryogenesis and during postgerminative growth" *Plant Physiology* 110: 1069-1079 (1996).

Zheng et al., "SPK1 is an essential S-phase-specific gene of *Saccharomyces cerevisiae* that encodes a nuclear serine/threonine/tyrosine kinase" *Mol. Cell Biol.* 13:5829-5842 (1993).

GenBank Accession No. NP 196718, dated Apr. 20, 2007.

Office Action from U.S. Appl. No. 11/180,418, document dated May 17, 2007, 11 pages; Sep. 17, 2007 Response to Office Action dated May 17, 2007, 8 pages.

Office Action from U.S. Appl. No. 11/357,357, document dated May 17, 2007, 9 pages; Sep. 17, 2007 Response to Office Action dated May 17, 2007, 6 pages.

Office Action from U.S. Appl. No. 11/362,546, document dated Nov. 15, 2006, 6 pages; Feb. 14, 2007 Response to Office Action dated Nov. 15, 2006, 5 pages.

Office Action from U.S. Appl. No. 11/362,546, document dated May 2, 2007, 6 pages; Jul. 2, 2007 Response to Final Office Action dated May 2, 2007, 4 pages.

Office Action from U.S. Appl. No. 11/369,193, document dated Nov. 15, 2006, 7 pages; Feb. 14, 2007 Response to Office Action dated Nov. 15, 2006, 5 pages.

Office Action from U.S. Appl. No. 11/369,173, document dated Nov. 15, 2006, 14 pages; Feb. 14, 2007 Response to Office Action dated Nov. 15, 2006, 6 pages.

Office Action from U.S. Appl. No. 11/369,173, document dated May 3, 2007, 9 pages.

Office Action from U.S. Appl. No. 11/370,240, dated Sep. 27, 2007, 8 pages.

Final Office Action from U.S. Appl. No. 11/357,357, dated Nov. 29, 2007, 9 pages.

Final Office Action from U.S. Appl. No. 11/180,418, dated Nov. 30, 2007, 10 pages.

Office Action from U.S. Appl. No. 11/370,253, dated Oct. 30, 2007, 20 pages.

Office Action from U.S. Appl. No. 11/371,356, dated Oct. 30, 2007, 20 pages.

Office Action from U.S. Appl. No. 11/371,624, dated Oct. 31, 2007, 21 pages.

Office Action from U.S. Appl. No. 11/396,357, dated Nov. 7, 2007, 7 pages.

Office Action from U.S. Appl. No. 11/371,623, dated Nov. 16, 2007, 10 pages.

Office Action from U.S. Appl. No. 11/369,168, dated Oct. 30, 2007, 20 pages.

Notice of Allowance from U.S. Appl. No. 11/367,760, dated Oct. 5, 2007, 6 pages.

Notice of Allowance from U.S. Appl. No. 11/153,185, dated Nov. 13, 2007, 7 pages.

Notice of Allowance from U.S. Appl. No. 11/372,369, dated Nov. 13, 2007, 7 pages.

NUCLEIC ACID SEQUENCES ENCODING ZINC FINGER PROTEINS

RELATED-APPLICATIONS

This application is a continuation-in-part of U.S. patent application Ser. No. 11/241,607 filed Sep. 30, 2005, which claims the benefit of priority to U.S. Provisional Patent Application No. 60/638,820 filed Dec. 22, 2004. The entire contents of these related applications are incorporated by reference in their entirety.

BACKGROUND

1. Technical Field

The present invention relates to isolated polynucleotides, polypeptides encoded thereby, and the use of those products for making transgenic plants or organisms, such as transgenic plants.

2. Background Information

There are more than 300,000 species of plants. They show a wide diversity of forms, ranging from delicate liverworts, adapted for life in a damp habitat, to cacti, capable of surviving in the desert. The plant kingdom includes herbaceous plants, such as corn, whose life cycle is measured in months, to the giant redwood tree, which can live for thousands of years. This diversity reflects the adaptations of plants to survive in a wide range of habitats. This is seen most clearly in the flowering plants (phylum Angiospermophyta), which are the most numerous, with over 250,000 species. They are also the most widespread, being found from the tropics to the arctic.

When the molecular and genetic basis for different plant characteristics are understood, a wide variety of polynucleotides, both endogenous polynucleotides and created variants, polypeptides, cells, and whole organisms, can be exploited to engineer old and new plant traits in a vast range of organisms including plants. These traits can range from the observable morphological characteristics, through adaptation to specific environments to biochemical composition and to molecules that the plants (organisms) exude. Such engineering can involve tailoring existing traits, such as increasing the production of taxol in yew trees, to combining traits from two different plants into a single organism, such as inserting the drought tolerance of a cactus into a corn plant. Molecular and genetic knowledge also allows the creation of new traits. For example, the production of chemicals and pharmaceuticals that are not native to particular species or the plant kingdom as a whole.

SUMMARY

The present invention relates to isolated polynucleotides, polypeptides encoded thereby, and the use of those products for making transgenic organisms, such as plants, bacteria, yeast, fungi and mammals, depending upon the desired characteristics.

In the field of agriculture and forestry, efforts are constantly being made to produce plants with improved characteristics, such as increased overall yield or increased yield of biomass or chemical components, in particular in order to guarantee the supply of the constantly increasing world population with food and to guarantee the supply of reproducible raw materials. Conventionally, people try to obtain plants with an increased yield by breeding, but this is time-consuming and labor-intensive. Furthermore, appropriate breeding programs must be performed for each relevant plant species.

Over the last two decades, progress has been made by the genetic manipulation of plants. That is, by introducing into plants recombinant nucleic acid molecules and expressing them as exogenous genes or using them to silence endogenous genes within these plants. Such approaches have the advantage of not usually being limited to one plant species, but being transferable to other plant species and other organisms as well. EP-A 0 511 979, for example, discloses that the expression of a prokaryotic asparagine synthetase in plant cells inter alia leads to an increase in biomass production. Similarly, WO 96/21737 describes the production of plants with increased yield from the expression of deregulated or unregulated fructose-1,6-bisphosphatase due to an increased rate of the photosynthesis. Nevertheless, there is still a need for generally applicable processes that lead to improved characteristics (such as yield) in relevant plants associated with a wide array of industrial purposes.

BRIEF DESCRIPTION OF THE TABLES

Nucleic acid and amino acid sequences are listed in Table 2; annotations relevant to the sequences shown in Table 2 are presented in Table 1. Each sequence corresponds to a clone number. Each clone number corresponds to at least one sequence in Table 2. Nucleotide sequences in Table 2 are "Maximum Length Sequences" (MLS) that are the sequence of an insert in a single clone.

Table 1 is a Reference Table which correlates each of the sequences and SEQ ID NOs in Table 2 with a corresponding Ceres clone number, Ceres sequence identifier, and other information about the individual sequence. Table 2 is a Sequence Table with the sequence of each nucleic acid and amino acid sequence.

In Table 1, each section begins with a line that identifies the corresponding internal Ceres clone by its ID number. Subsection (A) then provides information about the nucleotide sequence including the corresponding sequence in Table 2, and the internal Ceres sequence identifier ("Ceres seq_id"). Subsection (B) provides similar information about a polypeptide sequence, but additionally identifies the location of the start codon in the nucleotide sequence which codes for the polypeptide. Subsection (C) provides information (where present) regarding identified domains within the polypeptide and (where present) a name for the polypeptide. Finally, subsection (D) provides (where present) information concerning amino acids which are found to be related and have some sequence identity to the polypeptide sequences of Table 2. Those "related" sequences identified by a "gi" number are in the GenBank data base.

In Table 2, Xaa within an amino acid sequence denotes an ambiguous amino acid. An Xaa at the end of an amino acid sequence indicates a stop codon.

TABLE 1

Reference table.

Clone IDs: 766557
(Ac) cDNA SEQ
    Pat. Appln. SEQ ID NO: 1 (SEQ ID NO: 9369 in U.S. Provisional Patent Application No. 60/638,820)
        Ceres SEQ ID NO: 24727151
        SEQ 1 w. TSS:
        29, 33, 202, 295
        Clone ID 766557: 1 -> 1715
    PolyP SEQ
        Pat. Appln. SEQ ID NO: 2 (SEQ ID NO: 9370 in U.S. Provisional

TABLE 1-continued

Reference table.

Patent Application No. 60/638,820)
    Ceres SEQ ID NO 24727794
      Loc. SEQ ID NO 1: @ 427 nt.
    (C) Pred. PP Nom. & Annot.
      Zinc finger, C3HC4 type (RING finger)
      Loc. SEQ ID NO 2: 127 -> 178 aa.
    (Dp) Rel. AA SEQ
      Align. NO 62410
      gi No 50902106
      Desp.: P0414E03.20 [*Oryza sativa* (*japonica* cultivar-group)]
>gi|20160570|dbj|BAB89518.1| P0414E03.20 [*Oryza sativa* (*japonica*
cultivar-group)] >gi|20805170|dbj|BAB92839.1| P0529H11.12
[*Oryza sativa* (*japonica* cultivar-group)]
      % Idnt.: 71.2
      Align. Len.: 222
      Loc. SEQ ID NO 2: 25 -> 246 aa.
      Align. NO 62411
      gi No 30102534
      Desp.: At5g05830 [*Arabidopsis thaliana*]
>gi|9759108|dbj|BAB09677.1| unnamed protein product [*Arabidopsis
thaliana*] >gi|15239254|ref|NP_196202.1|
zinc finger (C3HC4-type RING finger) family protein
[*Arabidopsis thaliana*]
      % Idnt.: 55.3
      Align. Len.: 161
      Loc. SEQ ID NO 2: 90 -> 245 aa.
      Align. NO 62412
      gi No 9759231
      Desp.: unnamed protein product [*Arabidopsis thaliana*]
      % Idnt.: 51.6
      Align. Len.: 126
      Loc. SEQ ID NO 2: 121 -> 244 aa.
      Align. NO 62413
      gi No 54261717
      Desp.: At2g37950 [*Arabidopsis thaliana*]
>gi|4895189|gb|AAD32776.1| unknown protein [*Arabidopsis thaliana*]
>gi|25408580|pir||B84799 hypothetical protein At2g37950 [imported] -
*Arabidopsis thaliana* family protein [*Arabidopsis thaliana*]
      % Idnt.: 44.3
      Align. Len.: 167
      Loc. SEQ ID NO 2: 83 -> 244 aa.
      Align. NO 62414
      gi No 15237796
      Desp.: zinc finger (C3HC4-type RING finger) protein family
[*Arabidopsis thaliana*]
      % Idnt.: 53.3
      Align. Len.: 105
      Loc. SEQ ID NO 2: 142 -> 244 aa.
      Align. NO 62415
      gi No 21537129
      Desp.: unknown [*Arabidopsis thaliana*]
      % Idnt.: 53.3
      Align. Len.: 105
      Loc. SEQ ID NO 2: 142 -> 244 aa.
      Align. NO 62416
      gi No 53749327
      Desp.: unknown protein [*Oryza sativa* (*japonica* cultivar-group)]
      % Idnt.: 36.6
      Align. Len.: 142
      Loc. SEQ ID NO 2: 114 -> 244 aa.
      Align. NO 62417
      gi No 6759430
      Desp.: putative protein [*Arabidopsis thaliana*]
>gi|11290586|pir||T45947 hypothetical protein F7J8.50 - *Arabidopsis
thaliana* >gi|15240886|ref|NP_195727.1| zinc
finger (C3HC4-type RING finger) family protein [*Arabidopsis thaliana*]
      % Idnt.: 49
      Align. Len.: 104
      Loc. SEQ ID NO 2: 70 -> 173 aa.
      Align. NO 62418
      gi No 29725746
      Desp.: hypothetical protein [*Arabidopsis thaliana*]
>gi|42569605|ref|NP_180967.2| zinc finger (C3HC4-type RING finger)
family protein [*Arabidopsis thaliana*]
      % Idnt.: 36
      Align. Len.: 125
      Loc. SEQ ID NO 2: 124 -> 240 aa.

TABLE 1-continued

Reference table.

Align. NO 62419
      gi No 52076906
      Desp.: zinc finger (C3HC4-type RING finger) protein-like
[*Oryza sativa* (*japonica* cultivar-group)] >gi|52076620|dbj|BAD45521.1|
zinc finger (C3HC4-type RING finger) protein-like [*Oryza sativa*
(*japonica* cultivar-group)]
      % Idnt.: 32.4
      Align. Len.: 139
      Loc. SEQ ID NO 2: 99 -> 235 aa.

TABLE 2

Sequence listing.

```
<210> 1

<211> 1728

<212> DNA (genomic)

<213> Triticum aestivum

<220>

<221> misc_feature

<222> (1) . . . (1728)

<223> Ceres Seq. ID no. 24727151

<220>

<221> misc_feature

<222> () . . . ()

<223> n is a, c, t, g, unknown, or other

<400> 1
ATAAGACCAC GGTGAGCTGA GCTGACAGTG CCAAGCCAAA        60
CCCCTCCACA GTCTCTCCTC

CTCCTCCCGA CAAGCACAGA ACTCGTCTTT TCCTTTCTCC       120
CCCCTTCCTC TTTTCCCCTC

ACCTCACCTC ACTGTGCGGC GTGGCCACTG CCAGTACAAT       180
CCGCTCACTC TTTATTCCCT

CGGCTGCCCT TGTCTCGTTG CGTGTCCCTC CTGCGGTTAT       240
GGATCAAGAA ACCCTCACGAG

AACCCCGCCG CTTCAGCCGT ATATTGCCGC ATTAGTCGGG       300
GCCCAGCACT CGCCGGATCG

TTTCTCGCGA TCGCATTGCA TGCGCTCTTC CTGATCTCCG       360
ACGCGGATTG ATTTCATTTC

CGTCGCGTTG CCGGCGGCGG GATTCGGGGC CGCGGCATTT       420
TGTCTGGTTG AGGAAGAGGA

GGGGCAATGG TCGGCAGCGG CGCACAGTCG GCAAGCGGCG       480
CGGAGGTCGA AGACATCGAG

CTCGGCGAGC GGCGGCGCGC GGACGAGTTC GTGGACGACG       540
ACGAGGAGGG CAGCCAGTAC

TTCACGGACG CGGAGGACCG GTCGTGGCCC TCGCACTCGC       600
GCCAAGAGTC CGCCGCCTTC

GAGGACTGCA TCTCGCGGTG CGCCTCCACC CGCGCCAGCT       660
CCTGCGGCGG CGCCGACAGC

GACGCGGACA TCGAGGCCGG CGGCGGGCAC TTCAGGAAGT       720
CGTCGTGCGT GTCCGAGTGC
```

TABLE 2-continued

Sequence listing.

```
TCGCTGGACG ACGTCGACCT GGAGGCCGGG TTTGGCGGCG        780
AGAGCGCCAA GGGCAGCCCC

GACCCCGAGA AGGCCGAGAA GAACTGCCGC ATTTGCCACC        840
TCGGCCTGGA GAGCGCGGCG

GCCGAGTCCG GCGCCGGCAT CACGCTCGGC TGCTCCTGCA        900
AGGGCGACCT CTCCTACTCC

CACAAGCAGT GCGCCGAGAC CTGGTTCAAG ATCAGAGGCA        960
ACAAGACCTG TGAGATCTGC

AGCTCAACCG CATGCAATGT GGTTGTGTTA GGCGATCCGG       1020
AGTTTGTCGA GCAGTCGAAC

GAATCGAACA CCACAGCAGC TGGGCATACA TTTCCAAACG       1080
AAACCAGGAG ATTTTGGCAA

GGGCATCGGT TCCTCAACTT CCTTCTGGCA TGCATGGTCT       1140
TCGCCTTCGT CATCTCATGG

CTCTTCCACT TCAACGTCCC GGGGTGAGTT TCACGGCGGA       1200
CGGTCCCTCA ATAAAAAGCT

CCAAGGCCAT TACGGCAGCA ACATGTGGG TTAGGTTCAA        1260
CAAATCTGGA GAAACAGGCT

AAAAGGTTAA GTTAAGCTGT GAAGAGGTAC ACAAATATAT       1320
GGTCGGCGCG GCGGCCTTAA

ATTTGCCTTG ATCGGGGTTC AGTAGCACGA AGGAACCCT        1380
GATCAGGATC TCCTCCCGCC

CGCGTGCCCC AAGATTTGAG TGAAGATAGC GGCGAAGAAT       1440
GGAAGATGTG TTGTTGTTCG

CTTGTTCCGT GATTATTGTT GTCTTGGTTT GAAGAAGAAC       1500
AGGCTTATGT TAGCGTTGTC

ATTTCCTAGC TTTTTGCCGT TTTGCCTTGT GAGTTGGTGT       1560
GGTCTGTGTG TGCAGATTTC

TCTACGCCTG CCCTTTGTTC CAGTGTTTAT AGTCCTGATA       1620
AACAGGATGA GGTGGCAGCC

AGCTGTCCTT AGCAAGGAAA ATGTAGTGCC AGGTCAGTCC       1680
CGAACAAATG TTGCCGAAAT

AATCATGAGG AAATTATTGT GGAATGCTTG AGCTCAAAAA       1728
AAAAAAA
```

<210> 2

<211> 246

<212> PRT

<213> Triticum aestivum

<220>

<221> peptide

<222> (1)...(246)

<223> Ceres Seq. ID no. 24727794

<220>

<221> misc_feature

<222> ()...()

<223> xaa is any aa, unknown or other

<400> 2

```
Met Val Gly Ser Gly Ala Gln Ser Ala Ser Gly Ala
1               5                   10
Glu Val Glu Asp
        15
Ile Glu Leu Gly Glu Arg Arg Ala Asp Glu Phe
            20                  25
Val Asp Asp Asp
    30
Glu Glu Gly Ser Gln Tyr Phe Thr Asp Ala Glu Asp
                35                  40
Arg Ser Trp Pro
45
Ser His Ser Arg Gln Glu Ser Ala Ala Phe Glu Asp
        50                  55                  60
Cys Ile Ser Arg
Cys Ala Ser Thr Arg Ala Ser Ser Cys Gly Gly Ala
65                  70                  75
Asp Ser Asp Ala
        80
Asp Ile Glu Ala Gly Gly Gly His Phe Arg Lys Ser
                85                  90
Ser Cys Val Ser
    95
Glu Cys Ser Leu Asp Asp Val Asp Leu Glu Ala Gly
                100                 105
Phe Gly Gly Glu
110
Ser Ala Lys Gly Ser Pro Asp Pro Glu Lys Ala Glu
        115                 120
Lys Asn Cys Arg
125
Ile Cys His Leu Gly Leu Glu Ser Ala Ala Ala Glu
        130                 135                 140
Ser Gly Ala Gly
Ile Thr Leu Gly Cys Ser Cys Lys Gly Asp Leu Ser
145                 150                 155
Tyr Ser His Lys
        160
Gln Cys Ala Glu Thr Trp Phe Lys Ile Arg Gly Asn
                165                 170
Lys Thr Cys Glu
        175
Ile Cys Ser Ser Thr Ala Cys Asn Val Val Leu
                180                 185
Gly Asp Pro Glu
        190
Phe Val Glu Gln Ser Asn Glu Ser Asn Thr Thr Ala
            195                 200
Ala Gly His Thr
205
Phe Pro Asn Glu Thr Arg Arg Phe Trp Gln Gly His
    210                 215                 220
Arg Phe Leu Asn
Phe Leu Leu Ala Cys Met Val Phe Ala Phe Val Ile
225                 230                 235
Ser Trp Leu Phe
        240
His Phe Asn Val Pro Gly
                245
```

DETAILED DESCRIPTION

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptide that comprises the same domain(s). Domains also define areas of non-coding sequences such as promoters and miRNAs.

Endogenous: The term "endogenous," within the context of the current invention refers to any polynucleotide, polypeptide or protein sequence which is a natural part of a cell or organism regenerated from said cell.

Exogenous: "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. (1984) *EMBO J*. 3:141; Herrera-Estrella et al. (1983) *EMBO J*. 2:987; of monocots, representative papers are those by Escudero et al. (1996) *Plant J*. 10:355; Ishida et al. (1996) *Nature Biotechnology* 14:745; May et al. (1995) *Bio/Technology* 13:486), biolistic methods (Armaleo et al. (1990) *Current Genetics* 17:97), electroporation, in planta techniques, and the like. The term "exogenous" as used herein is also intended to encompass inserting a naturally found element into a non-naturally found location.

Gene: The term "gene," as used in the context of the current invention, encompasses all regulatory and coding sequence contiguously associated with a single hereditary unit with a genetic function. Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes comprised of "exons" (coding sequences), which may be interrupted by "introns" (non-coding sequences), encode proteins. A gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, artificial chromosome, plasmid, vector, etc., or as a separate isolated entity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Homologous gene: In the current invention, "homologous gene" refers to a gene that shares sequence similarity with the gene of interest. This similarity may be in only a fragment of the sequence and often represents a functional domain such as, examples including without limitation a DNA binding domain, a domain with tyrosine kinase activity, or the like. The functional activities of homologous genes are not necessarily the same.

Misexpression: The term "misexpression" refers to an increase or a decrease in the transcription of a coding region into a complementary RNA sequence as compared to the parental wild-type. This term also encompasses expression of a gene or coding region for a different time period as compared to the wild-type and/or from a non-natural location within the plant genome.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981) *Add. APL. Math*. 2:482, by the homology alignment algorithm of Needleman and Wunsch (1970) *J. Mol. Biol*. 48:443, by the search for similarity method of Pearson and Lipman (1988) *Proc. Natl. Acad. Sci*. (USA) 85: 2444, by computerized implementations of algorithms such as GAP, BESTFIT, BLAST, PASTA, and TFASTA (Accelrys, Inc., 10188 Telesis Court, Suite 100 San Diego, Calif. 92121) or by inspection. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Regulatory Sequence: The term "regulatory sequence," as used in the current invention, refers to any nucleotide sequence that influences transcription or translation initiation and rate, and stability and/or mobility of the transcript or polypeptide product. Regulatory sequences include, but are not limited to, promoters, promoter control elements, protein binding sequences, 5' and 3' UTRs, transcriptional start site, termination sequence, polyadenylation sequence, introns, certain sequences within a coding sequence, etc.

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$-5° C. to $T_m$-10° C. Medium or moderate stringency conditions are those providing $T_m$-20° C. to $T_m$-29° C. Low stringency conditions are those providing a condition of $T_m$-40° C. to $T_m$-48° C. The relationship of hybridization conditions to $T_m$ (in ° C.) is expressed in the mathematical equation $$T_m = 81.5 - 16.6(\log_{10}[Na^+]) + 0.41(\% \ G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log \{[Na^+]/(1+0.7[Na^+])\} + 0.41 (\% \ G+C) - 500/L \ 0.63(\% formamide) \quad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al. (1973) *J. Mol. Biol.* 81:123), stringency conditions in polynucleotide hybridization reactions can be adjusted to favor hybridization of polynucleotides from identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency conditions can be selected during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene or DNA sequence can be considered substantially free of other plant genes or DNA sequences.

Translational start site: In the context of the current invention, a "translational start site" is usually an ATG in the cDNA transcript, more usually the first ATG. A single cDNA, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single gene may have multiple transcriptional start sites, some of which may be specific for transcription in a particular cell-type or tissue.

Untranslated region (UTR): A "UTR" is any contiguous series of nucleotide bases that is transcribed, but is not translated. These untranslated regions may be associated with particular functions such as increasing mRNA message stability. Examples of UTRs include, but are not limited to polyadenylation signals, terminations sequences, sequences located between the transcriptional start site and the first exon (5' UTR) and sequences located between the last exon and the end of the mRNA (3' UTR).

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc).

Characteristics of Polynucleotides

The genes and polynucleotides of the present invention are of interest because when they are misexpressed (i.e., when over expressed at a non-natural location or in an increased amount) or when they allow silencing endogenous genes, they can produce plants with important modified characteristics as discussed below. These traits can be used to exploit or maximize plant products or to minimize undesirable characteristics. For example, an increase in plant height is beneficial in species grown or harvested for their main stem or trunk, such as ornamental cut flowers, fiber crops (e.g. flax, kenaf, hesperaloe, hemp) and wood producing trees. Increase in inflorescence thickness is also desirable for some ornamentals, while increases in the number, shape and size of leaves can lead to increased production/harvest from leaf crops such as lettuce, spinach, cabbage, switch grass and tobacco. Likewise, a decrease in plant height is beneficial in species that are particularly susceptible to lodging or uprooting due to wind stress.

The polynucleotides and polypeptides of the invention were isolated from different plant species as noted in Table 2 or the Sequence Listing provided in any of the priority applications. The polynucleotides and polypeptides are useful to confer on transgenic plants the properties identified for each sequence in the relevant portion (miscellaneous feature section) of Table 1, Table 2, or the Sequence Listing provided in any of the priority applications. The miscellaneous feature section of Table 1, Table 2, or the Sequence Listing provided in any of the priority applications can contain, for each sequence, a description of the domain or other characteristic from which the sequence has the function known in the art for other sequences. Some identified domains are indicated with "PFam Name", signifying that the pfam name and description can be found in the pfam database available via the internet. Other domains are indicated by reference to a "GI Number" from the public sequence database maintained by GenBank under the NCBI, including the non-redundant (NR) database.

The sequences of the invention can be applied to substrates for use in microarray applications such as, but not limited to, assays of global gene expression under varying development and growth conditions. The microarrays are also used for diagnostic or forensic purposes. Arrays can be produced using different procedures such as those from Affymetrix or Agilent. Protocols for these procedures can be obtained from these companies or found via the internet.

The polynucleotides, or fragments thereof, can also be used as probes and primers. Probe length varies depending on the application. For use as primers, probes are 12-40 nucleotides, preferably 18-30 nucleotides long. For use in mapping, probes are preferably 50 to 500 nucleotides, preferably 100-250 nucleotides long. For Southern hybridizations, probes as long as several kilobases are used.

The probes and/or primers are produced by synthetic procedures such as the triester method of Matteucci et al. (1981) *J. Am. Chem. Soc.* 103:3185 or according to Urdea et al. (1981) *Proc. Natl. Acad.* 80:7461 or using commercially available automated oligonucleotide synthesizers.

The polynucleotides of the invention can be utilized in a number of methods known to those skilled in the art as probes and/or primers to isolate and detect polynucleotides including, without limitation: Southerns, Northerns, Branched DNA hybridization assays, polymerase chain reaction microarray assays and variations thereof. Specific methods given by way of examples, and discussed below include: hybridization, methods of mapping, Southern blotting, isolating cDNA from related organisms, and isolating and/or identifying homologous and orthologous genes.

Also, the nucleic acid molecules of the invention can be used in other methods, such as high density oligonucleotide hybridizing assays, described, for example, in U.S. Pat. Nos. 6,004,753 and 5,945,306.

The polynucleotides or fragments thereof of the present invention can be used as probes and/or primers for detection and/or isolation of related polynucleotide sequences through hybridization. Hybridization of one nucleic acid to another constitutes a physical property that defines the polynucleotide of the invention and the identified related sequences. Also, such hybridization imposes structural limitations on the pair. A good general discussion of the factors for determining hybridization conditions is provided by Sambrook et al. ("Molecular Cloning, a Laboratory Manual," 2nd ed., c. 1989 by Cold Spring Harbor Laboratory Press, Cold Spring Harbor, N.Y.; see esp., chapters 11 and 12). Additional considerations and details of the physical chemistry of hybridization are provided by G. H. Keller and M. M. Manak "DNA Probes," $2^{nd}$ Ed. pp. 1-25, c. 1993 by Stockton Press, New York, N.Y.

When using the polynucleotides to identify homologous genes in other species, the practitioner will preferably adjust the amount of target DNA of each species so that, as nearly as is practical, the same number of genome equivalents are present for each species examined. This prevents faint signals from species having large genomes, and thus small numbers of genome equivalents per mass of DNA, from erroneously being interpreted as absence of the corresponding gene in the genome.

The probes and/or primers of the instant invention can also be used to detect or isolate nucleotides that are "identical" to the probes or primers. Two nucleic acid sequences or polypeptides are said to be "identical" if the sequence of nucleotides or amino acid residues, respectively, in the two sequences is the same when aligned for maximum correspondence as described below.

Isolated polynucleotides within the scope of the invention also include allelic variants of the specific sequences presented in Table 1, Table 2, or the Sequence Listing provided in any of the priority applications. The probes and/or primers of the invention are also used to detect and/or isolate polynucleotides exhibiting at least 80% sequence identity with a sequence of Table 1, Table 2, or the Sequence Listing provided in any of the priority applications or a fragment thereof. Related polynucleotide sequences can also be identified according to the methods described in U.S. Patent Publication 20040137466A1, dated Jul. 15, 2004 to Jofuku et al.

With respect to nucleotide sequences, degeneracy of the genetic code provides the possibility to substitute at least one nucleotide of the nucleotide sequence of a gene with a different nucleotide without changing the amino acid sequence of the polypeptide. Hence, the DNA of the present invention also has any base sequence that has been changed from a sequence of Table 1, Table 2, or the Sequence Listing provided in any of the priority applications by substitution in accordance with degeneracy of genetic code. References describing codon usage include: Carels et al. (1998) *J. Mol. Evol.* 46: 45 and Fennoy et al. (1993) *Nucl. Acids Res.* 21(23): 5294.

The polynucleotides of the invention are also used to create various types of genetic and physical maps of the genome of the plant species listed in Table 1, Table 2, or the Sequence Listing provided in any of the priority applications. Some are absolutely associated with particular phenotypic traits, allowing construction of gross genetic maps. Creation of such maps is based on differences or variants, generally referred to as polymorphisms, between different parents used in crosses. Common methods of detecting polymorphisms that can be used are restriction fragment length polymorphisms (RFLPs), single nucleotide polymorphisms (SNPs) or simple sequence repeats (SSRs).

The use of RFLPs and of recombinant inbred lines for such genetic mapping is described for *Arabidopsis* by Alonso-Blanco et al. (*Methods in Molecular Biology*, vol. 82, "*Arabidopsis* Protocols", pp. 137-146, J. M. Martinez-Zapater and J. Salinas, eds., c. 1998 by Humana Press, Totowa, N.J.) and for corn by Burr ("Mapping Genes with Recombinant Inbreds", pp. 249-254. In Freeling, M. and V. Walbot (Ed.), *The Maize Handbook*, c. 1994 by Springer-Verlag New York, Inc.: New York, N.Y., USA; Berlin Germany; Burr et al. *Genetics* (1998) 118: 519; Gardiner, J. et al. (1993) *Genetics* 134: 917). This procedure, however, is not limited to plants and is used for other organisms (such as yeast) or for individual cells.

The polynucleotides of the present invention are also used for simple sequence repeat (SSR) mapping. Rice SSR mapping is described by Morgante et al. (*The Plant Journal* (1993) 3: 165), Panaud et al. (*Genome* (1995) 38: 1170); Senior et al. (*Crop Science* (1996) 36: 1676), Taramino et al. (*Genome* (1996) 39: 277) and Ahn et al. (*Molecular and General Genetics* (1993)241: 483-90). SSR mapping is achieved using various methods. In one instance, polymorphisms are identified when sequence specific probes contained within a polynucleotide flanking an SSR are made and used in polymerase chain reaction (PCR) assays with template DNA from two or more individuals of interest. Here, a change in the number of tandem repeats between the SSR-flanking sequences produces differently sized fragments (U.S. Pat. No. 5,766,847). Alternatively, polymorphisms are identified by using the PCR fragment produced from the SSR-flanking sequence specific primer reaction as a probe against Southern blots representing different individuals (U. H. Refseth et al. (1997) *Electrophoresis* 18: 1519).

The polynucleotides of the invention can further be used to identify certain genes or genetic traits using, for example, known AFLP technologies, such as in EP0534858 and U.S. Pat. No. 5,878,215.

The polynucleotides of the present invention are also used for single nucleotide polymorphism (SNP) mapping.

Genetic and physical maps of crop species have many uses. For example, these maps are used to devise positional cloning strategies for isolating novel genes from the mapped crop species. In addition, because the genomes of closely related species are largely syntenic (i.e., they display the same ordering of genes within the genome), these maps are used to isolate novel alleles from relatives of crop species by positional cloning strategies.

The various types of maps discussed above are used with the polynucleotides of the invention to identify Quantitative Trait Loci (QTLs). Many important crop traits, such as the solids content of tomatoes, are quantitative traits and result from the combined interactions of several genes. These genes reside at different loci in the genome, often times on different chromosomes, and generally exhibit multiple alleles at each locus. The polynucleotides of the invention are used to identify QTLs and isolate specific alleles as described by de Vicente and Tanksley (*Genetics* (1993) 134:585). Once a desired allele combination is identified, crop improvement is accomplished either through biotechnological means or by directed conventional breeding programs (for review see Tanksley and McCouch (1997) *Science* 277:1063). In addition to isolating QTL alleles in present crop species, the polynucleotides of the invention are also used to isolate alleles from the corresponding QTL of wild relatives.

In another embodiment, the polynucleotides are used to help create physical maps of the genome of the plant species mentioned in Table 1, Table 2, or the Sequence Listing provided in any of the priority applications and related species thereto. Where polynucleotides are ordered on a genetic map, as described above, they are used as probes to discover which clones in large libraries of plant DNA fragments in YACs, BACs, etc. contain the same polynucleotide or similar sequences, thereby facilitating the assignment of the large DNA fragments to chromosomal positions. Subsequently, the large BACs, YACs, etc. are ordered unambiguously by more detailed studies of their sequence composition (e.g., Marra et al. (1997) Genomic Research, 7:1072-1084) and by using their end or other sequences to find the identical sequences in other cloned DNA fragments. The overlapping of DNA sequences in this way allows building large contigs of plant sequences to be built that, when sufficiently extended, provide a complete physical map of a chromosome. Sometimes the polynucleotides themselves provide the means of joining cloned sequences into a contig. All scientific and patent publications cited in this paragraph are hereby incorporated by reference.

U.S. Pat. Nos. 6,287,778 and 6,500,614, both hereby incorporated by reference, describe scanning multiple alleles of a plurality of loci using hybridization to arrays of oligonucleotides. These techniques are useful for each of the types of mapping discussed above.

Following the procedures described above and using a plurality of the polynucleotides of the present invention, any individual is genotyped. These individual genotypes are used for the identification of particular cultivars, varieties, lines, ecotypes and genetically modified plants or can serve as tools for subsequent genetic studies involving multiple phenotypic traits.

Identification and isolation of orthologous genes from closely related species and alleles within a species is particularly desirable because of their potential for crop improvement. Many important crop traits result from the combined interactions of the products of several genes residing at different loci in the genome. Generally, alleles at each of these loci make quantitative differences to the trait. Once a more favorable allele combination is identified, crop improvement is accomplished either through biotechnological means or by directed conventional breeding programs (Tanksley et al., (1997) *Science* 277:1063).

Use of the Genes to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector, and which are suitable for transformation of plant cells. The construct is made using standard recombinant DNA techniques (Sambrook et al. 1989) and is introduced to the species of interest by *Agrobacterium*-mediated transformation or by other means of transformation as referenced below.

The sequences of the present invention can be in sense orientation or in anti-sense orientation.

If a decrease in the transcription or translation product of an endogenous gene (gene silencing) is desired, the sequence of interest is transcribed as an antisense nucleic acid or an interfering RNA similar or identical to part of the endogenous gene. Antisense nucleic acids or interfering RNAs are about 10 nucleotides to about 2,500 nucleotides in length. For example, the nucleic acid of the present invention can be used as an antisense nucleic acid to its corresponding endogenous gene. Alternatively, the transcription product of a nucleic acid of the invention can be similar or identical to the sense coding sequence of its corresponding endogenous gene, but is an RNA that is unpolyadenylated, lacks a 5' cap structure, or contains an unsplicable intron. The nucleic acid of the present invention in sense orientation can also be used as a partial or full-length coding sequence that results in inhibition of the expression of an endogenous polypeptide by co-suppression. Methods of co-suppression using a full-length cDNA sequence as well as a partial cDNA sequence are known in the art (see, for example, U.S. Pat. No. 5,231,020).

Alternatively, a nucleic acid can be transcribed into a ribozyme that affects expression of an mRNA (see, U.S. Pat. No. 6,423,885). Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art (see, for example, U.S. Pat. No. 5,254,678). Hammerhead ribozyme sequences can be embedded in a stable RNA such as a transfer RNA (tRNA) to increase cleavage efficiency in vivo (Perriman et al. (1995) *Proc. Natl. Acad. Sci. USA*, 92(13):6175-6179; de Feyter and Gaudron *Methods in Molecular Biology*, Vol. 74, Chapter 43, "Expressing Ribozymes in Plants," Edited by Turner, P. C, Humana Press Inc., Totowa, N.J.). RNA endoribonucleases such as the one that occurs naturally in *Tetrahymena thermophila* and which have been described extensively by Cech and collaborators can also be useful (see, for example, U.S. Pat. No. 4,987, 071).

A nucleic acid of the present invention can also be used for its transcription into an interfering RNA. Such an RNA can be one that can anneal to itself, for example a double stranded RNA having a stem-loop structure. One strand of the stem portion of a double stranded RNA can comprise a sequence that is similar or identical to the sense coding sequence of an endogenous polypeptide and that is about 10 nucleotides to about 2,500 nucleotides in length. Generally, the length of the nucleic acid sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA can comprise an antisense sequence of an endogenous polypeptide and can have a length that is shorter, the same as, or longer than the length of the corresponding sense sequence. The loop portion of a double stranded RNA can be from 10 nucleotides to 500 nucleotides in length, for example from 15 nucleotides to 100 nucleotides, from 20 nucleotides to 300 nucleotides or from 25 nucleotides to 400 nucleotides in length. The loop portion of the RNA can include an intron (see, for example the following publications: WO 98/53083; WO 99/32619; WO 98/36083; WO 99/53050; US 20040214330; U.S. Patent Application Publication No. 20030180945; U.S. Pat. No. 5,034,323; U.S. Pat. No. 6,452,067; U.S. Pat. No. 6,777,588; U.S. Pat. No. 6,573,099 and U.S. Pat. No. 6,326,527). Interfering RNA also can be constructed as described in Brummell, et al. (2003) Plant J. 33:793-800.

The vector backbone for the recombinant constructs is any of those typical in the art such as plasmids (such as Ti plasmids), viruses, artificial chromosomes, BACs, YACs and PACs and vectors of the sort described by:

(a) BAC: Shizuya et al. (1992) *Proc. Natl. Acad. Sci. USA* 89: 8794-8797; Hamilton et al. (1996) *Proc. Natl. Acad. Sci. USA* 93: 9975-9979;
(b) YAC: Burke et al. (1987) *Science* 236:806-812;
(c) PAC: Sternberg N. et al. (1990) *Proc. Natl. Acad. Sci. USA*. Jan; 87(1):103-7;
(d) Bacteria-Yeast Shuttle Vectors: Bradshaw et al. (1995) *Nucl. Acids Res*. 23: 4850-4856;
(e) Lambda Phage Vectors: Replacement Vector, e.g., Frischauf et al. (1983) *J. Mol. Biol.*, 170: 827-842; or Insertion vector, e.g., Huynh et al., In: Glover N M (ed) DNA Cloning: A practical Approach, Vol. 1 Oxford: IRL Press (1985); T-DNA gene fusion vectors: Walden et al. (1990) *Mol. Cell. Biol.*, 1: 175-194; and
(g) Plasmid vectors: Sambrook et al., infra.

Typically, the construct comprises a vector containing a sequence of the present invention with any desired transcriptional and/or translational regulatory sequences, such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron, glyphosate or phosphinotricin.

A plant promoter fragment is used that directs transcription of the gene in all tissues of a regenerated plant and/or is a constitutive promoter. Alternatively, the plant promoter directs transcription of a sequence of the invention in a specific tissue (tissue-specific promoter) or is otherwise under more precise environmental control, such as chemicals, cold, heat, drought, salt and many others (inducible promoter).

If proper polypeptide production is desired, a polyadenylation region at the 3'-end of the coding region is typically included. The polyadenylation region is derived from the natural gene, from a variety of other plant genes, or from T-DNA, synthesized in the laboratory.

Transformation

Techniques for transforming a wide variety of higher plant species are well known and described in the technical and scientific literature. See, e.g. Weising et al. (1988) *Ann. Rev. Genet*. 22:421 and Christou (1995) Euphytica, v. 85, n.1-3:13-27.

The person skilled in the art knows processes for the transformation of monocotyledonous and dicotyledonous plants. A variety of techniques are available for introducing DNA into a plant host cell. These techniques comprise transformation of plant cells by DNA injection, DNA electroporation, use of bolistics methods, protoplast fusion and via T-DNA using *Agrobacterium tumefaciens* or *Agrobacterium rhizogenes*, as well as further possibilities, or other bacterial hosts for Ti plasmid vectors. See, for example, Broothaerts et al. (2005) Gene Transfer to Plants by Diverse Species of Bacteria, *Nature*, Vol. 433, pp. 629-633.

DNA constructs of the invention are introduced into the cell or the genome of the desired plant host by a variety of conventional techniques. For example, the DNA construct is introduced using techniques such as electroporation, microinjection and polyethylene glycol precipitation of plant cell protoplasts or protoplast fusion. Electroporation techniques are described in Fromm et al. (1985) *Proc. Natl. Acad. Sci. USA* 82:5824. Microinjection techniques are known in the art and well described in the scientific and patent literature. The plasmids do not have to fulfill specific requirements for use in DNA electroporation or DNA injection into plant cells. Simple plasmids such as pUC derivatives can be used.

The introduction of DNA constructs using polyethylene glycol precipitation is described in Paszkowski et al. (1984) *EMBO J*. 3:2717. Introduction of foreign DNA using protoplast fusion is described by Willmitzer (Willmitzer, L. (1993) Transgenic plants. In: Biotechnology, A Multi-Volume Comprehensive Treatise (H. J. Rehm, G. Reed, A. Pühler, P. Stadler, eds.), Vol. 2, 627-659, VCH Weinheim-New York-Basel-Cambridge).

Alternatively, the DNA constructs of the invention are introduced directly into plant tissue using ballistic methods, such as DNA particle bombardment. Ballistic transformation techniques are described in Klein et al. (1987) *Nature* 327:773. Introduction of foreign DNA using ballistics is described by Willmitzer (Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627-659, VCH Weinheim-New York-Basel-Cambridge).

DNA constructs are also introduced with the help of *Agrobacteria*. The use of *Agrobacteria* for plant cell transformation is extensively examined and sufficiently disclosed in the specification of EP-A 120 516, and in Hoekema (In: The Binary Plant Vector System Offsetdrukkerij Kanters B. V., Alblasserdam (1985), Chapter V), Fraley et al. (Crit. Rev. Plant. Sci. 4, 1-46) and DePicker et al. (*EMBO J*. 4 (1985), 277-287). Using this technique, the DNA constructs of the invention are combined with suitable T-DNA flanking regions and introduced into a conventional *Agrobacterium tumefaciens* host vector. The virulence functions of the *Agrobacterium tumefaciens* host direct the insertion of the construct and adjacent marker(s) into the plant cell DNA when the cell is infected by the bacteria (McCormac et al. (1997) *Mol. Biotechnol.* 8:199; Hamilton (1997) *Gene* 200: 107; Salomon et al. (1984) *EMBO J.* 3:141; Herrera-Estrella et al. (1983) *EMBO J.* 2:987). *Agrobacterium tumefaciens*-mediated transformation techniques, including disarming and use of binary or co-integrate vectors, are well described in the scientific literature. See, for example Hamilton (1997) *Gene* 200:107; Müller et al. (1987) *Mol. Gen. Genet.* 207: 171; Komari et al. (1996) *Plant J.* 10: 165; Venkateswarlu et al. (1991) *Biotechnology* 9:1103 and Gleave (1992) *Plant Mol. Biol.* 20:1203; Graves and Goldman (1986) *Plant Mol. Biol.* 7:34 and Gould et al. (1991) *Plant Physiology* 95:426.

For plant cell T-DNA transfer of DNA, plant organs, e.g. infloresences, plant explants, plant cells that have been cultured in suspension or protoplasts are co-cultivated with *Agrobacterium tumefaciens* or *Agrobacterium rhizogenes* or other suitable T-DNA hosts. Whole plants are regenerated from the infected plant material or seeds generated from infected plant material using a suitable medium that contains antibiotics or biocides for the selection of transformed cells or by spraying the biocide on plants to select the transformed plants. Plants obtained in this way are then examined for the presence of the DNA introduced. The transformation of dicotyledonous plants via Ti-plasmid-vector systems and *Agrobacterium tumefaciens* is well established.

Monocotyledonous plants are also transformed by means of *Agrobacterium* based vectors (See, Chan et al. (1993) *Plant Mol. Biol.* 22: 491-506; Hiei et al. (1994) *Plant J.* 6:271-282; Deng et al. (1990) *Science in China* 33:28-34; Wilmink et al. *Plant* (1992) Cell Reports 11:76-80; May et al. (1995) *Bio/Technology* 13:486-492; Conner and Domisse (1992) *Int. J. Plant Sci.* 153:550-555; Ritchie et al. (1993) *Transgenic Res.* 2:252-265). Maize transformation in particular is described in the literature (see, for example, WO95/06128, EP 0 513 849; EP 0 465 875; Fromm et al., (1990) *Biotechnology* 8:833-844; Gordon-Kamm et al. (1990) *Plant Cell* 2:603-618; Koziel et al. (1993) *Biotechnology* 11:194-200). In EP292435 and in Shillito et al. (*Bio/Technology* (1989) 7:581) fertile plants are obtained from a mucus-free, soft (friable) maize callus. Prioli and Söndahl (*Bio/Technology* (1989) 7, 589) also report regenerating fertile plants from maize protoplasts of the maize Cateto inbred line, Cat 100-1.

Other cereal species have also been successfully transformed, such as barley (Wan and Lemaux, see above; Ritala et al., see above) and wheat (Nehra et al. (1994) *Plant J.* 5, 285-297).

Alternatives to *Agrobacterium* transformation for plants are ballistics, protoplast fusion, electroporation of partially permeabilized cells and use of glass fibers (See, Wan and Lemaux (1994) *Plant Physiol.* 104:37-48; Vasil et al. (1993) *Bio/Technology* 11: 1553-1558; Ritala et al. (1994) *Plant Mol. Biol.* 24:317-325; Spencer et al. (1990) *Theor. Appl. Genet.* 79:625-631).

Introduced DNA is usually stable after integration into the plant genome and is transmitted to the progeny of the transformed cell or plant. Generally the transformed plant cell contains a selectable marker that makes the transformed cells resistant to a biocide or an antibiotic such as kanamycin, G 418, bleomycin, hygromycin, phosphinotricin or others. Therefore, the individually chosen marker should allow the selection of transformed cells from cells lacking the introduced DNA.

The transformed cells grow within the plant in the usual way (McCormick et al. (1986) *Plant Cell Reports* 5, 81-84) and the resulting plants are cultured normally. Transformed plant cells obtained by any of the above transformation techniques are cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences.

Plant regeneration from cultured protoplasts is described in Evans et al., *Protoplasts Isolation and Culture* in "Handbook of Plant Cell Culture," pp. 124-176, MacMillan Publishing Company, New York, 1983; and Binding, *Regeneration of Plants, Plant Protoplasts*, pp. 21-73, CRC Press, Boca Raton, 1988. Regeneration also occurs from plant callus, explants, organs, or parts thereof. Such regeneration techniques are described generally in Klee et al. (1987) *Ann. Rev. of Plant Phys.* 38:467. Regeneration of monocots (rice) is described by Hosoyama et al. (*Biosci. Biotechnol. Biochem.* (1994) 58:1500) and by Ghosh et al. (*J. Biotechnol.* (1994) 32:1). Useful and relevant procedures for transient expression are also described in U.S. Provisional Patent Application No. 60/537,070 filed on Jan. 16, 2004 and PCT Application No. PCT/US2005/001153 filed on Jan. 14, 2005.

After transformation, seeds are obtained from the plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleotide sequences according to the invention generally encode an appropriate protein from any organism, in particular from plants, fungi, bacteria or animals. The sequences preferably encode proteins from plants or fungi. Preferably, the plants are higher plants, in particular starch or oil storing useful plants, such as potato or cereals such as rice, maize, wheat, barley, rye, triticale, oat, millet, etc., as well as spinach, tobacco, sugar beet, soya, cotton etc.

In principle, the process according to the invention can be applied to any plant. Therefore, monocotyledonous as well as dicotyledonous plant species are particularly suitable. The process is preferably used with plants that are interesting for agriculture, horticulture, biomass for conversion, textile, plants as chemical factories and/or forestry.

Thus, the invention has use over a broad range of plants, preferably higher plants, pertaining to the classes of *Angiospermae* and *Gymnospermae*. Plants of the subclasses of the *Dicotylodenae* and the *Monocotyledonae* are particularly suitable. Dicotyledonous plants belong to the orders of the *Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales,*

Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

Examples of species represented in these orders are tobacco, oilseed rape, sugar beet, potato, tomato, lettuce, cucumber, pepper, bean, pea, citrus fruit, apple, pear, berries, plum, melon, eggplant, cotton, soybean, sunflower, rose, poinsettia, petunia, guayule, cabbage, spinach, alfalfa, artichoke, corn, wheat, rye, barley, grasses such as switch grass or turf grass, millet, hemp, banana, poplar, eucalyptus trees, conifers.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

SEQUENCE LISTING

<160> NUMBER OF SEQ ID NOS: 2

<210> SEQ ID NO 1
<211> LENGTH: 1728
<212> TYPE: DNA
<213> ORGANISM: Triticum aestivum

<400> SEQUENCE: 1

```
ataagaccac ggtgagctga gctgacagtg ccaagccaaa cccctccaca gtctctcctc      60
ctcctcccga caagcacaga actcgtcttt tcctttctcc cccttcctc ttttcccctc     120
acctcacctc actgtgcggc gtggccactg ccagtacaat ccgctcactc tttattccct    180
cggctgccct tgtctcgttg cgtgtccctc ctgcggttat ggatcaagaa acctcacgag    240
aaccccgccg cttcagccgt atattgccgc attagtcggg gcccagcact cgccggatcg    300
tttctcgcga tcgcattgca tgcgctcttc ctgatctccg acgcggattg atttcatttc    360
cgtcgcgttg ccggcggcgg gattcggggc cgcggcattt tgtctggttg aggaagagga    420
ggggcaatgg tcggcagcgg cgcacagtcg gcaagcggcg cggaggtcga agacatcgag    480
ctcggcgagc ggcggcgcgc ggacgagttc gtggacgacg acgaggaggg cagccagtac    540
ttcacggacg cggaggaccg gtcgtggccc tcgcactcgc gccaagagtc cgccgccttc    600
gaggactgca tctcgcggtg cgcctccacc cgcgccagct cctgcggcgg cgccgacagc    660
gacgcggaca tcgaggccgg cggcgggcac ttcaggaagt cgtcgtgcgt gtccgagtgc    720
tcgctggacg acgtcgacct ggaggccggg tttggcggcg agagcgccaa gggcagcccc    780
gaccccgaga aggccgagaa gaactgccgc atttgccacc tcggcctgga gagcgcggcg    840
gccgagtccg gcgccggcat cacgctcggc tgctcctgca agggcgacct ctcctactcc    900
cacaagcagt gcgccgagac ctggttcaag atcagaggca acaagacctg tgagatctgc    960
agctcaaccg catgcaatgt ggttgtgtta ggcgatccgg agtttgtcga gcagtcgaac   1020
gaatcgaaca ccacagcagc tgggcataca tttccaaacg aaaccaggag attttggcaa   1080
gggcatcggt tcctcaactt ccttctggca tgcatggtct tcgccttcgt catctcatgg   1140
ctcttccact tcaacgtccc ggggtgagtt tcacggcgga cggtccctca ataaaaagct   1200
ccaaggccat tacggcagca aacatgtggg ttaggttcaa caaatctgga gaaacaggct   1260
aaaaggttaa gttaagctgt gaagaggtac acaaatatat ggtcggcgcg gcggccttaa   1320
atttgccttg atcggggttc agtagcacga aaggaaccct gatcaggatc tcctcccgcc   1380
cgcgtgcccc aagatttgag tgaagatagc ggcgaagaat ggaagatgtg ttgttgttcg   1440
cttgttccgt gattattgtt gtcttggttt gaagaagaac aggcttatgt tagcgttgtc   1500
```

```
atttcctagc tttttgccgt tttgccttgt gagttggtgt ggtctgtgtg tgcagatttc    1560
tctacgcctg cccttttgttc cagtgtttat agtcctgata acaggatga ggtggcagcc    1620 agctgtcctt agcaaggaaa atgtagtgcc aggtcagtcc cgaacaaatg ttgccgaaat    1680
aatcatgagg aaattattgt ggaatgcttg agctcaaaaa aaaaaaaa               1728
```

<210> SEQ ID NO 2
<211> LENGTH: 246
<212> TYPE: PRT
<213> ORGANISM: Triticum aestivum

<400> SEQUENCE: 2

```
Met Val Gly Ser Gly Ala Gln Ser Ala Ser Gly Ala Glu Val Glu Asp
 1               5                  10                  15

Ile Glu Leu Gly Glu Arg Arg Ala Asp Glu Phe Val Asp Asp Asp
                20                  25                  30

Glu Glu Gly Ser Gln Tyr Phe Thr Asp Ala Glu Asp Arg Ser Trp Pro
             35                  40                  45

Ser His Ser Arg Gln Glu Ser Ala Ala Phe Glu Asp Cys Ile Ser Arg
 50                  55                  60

Cys Ala Ser Thr Arg Ala Ser Ser Cys Gly Gly Ala Asp Ser Asp Ala
 65                  70                  75                  80

Asp Ile Glu Ala Gly Gly Gly His Phe Arg Lys Ser Ser Cys Val Ser
             85                  90                  95

Glu Cys Ser Leu Asp Asp Val Asp Leu Glu Ala Gly Phe Gly Gly Glu
            100                 105                 110

Ser Ala Lys Gly Ser Pro Asp Pro Glu Lys Ala Glu Lys Asn Cys Arg
            115                 120                 125

Ile Cys His Leu Gly Leu Glu Ser Ala Ala Ala Glu Ser Gly Ala Gly
            130                 135                 140

Ile Thr Leu Gly Cys Ser Cys Lys Gly Asp Leu Ser Tyr Ser His Lys
145                 150                 155                 160

Gln Cys Ala Glu Thr Trp Phe Lys Ile Arg Gly Asn Lys Thr Cys Glu
                165                 170                 175

Ile Cys Ser Ser Thr Ala Cys Asn Val Val Val Leu Gly Asp Pro Glu
            180                 185                 190

Phe Val Glu Gln Ser Asn Glu Ser Asn Thr Thr Ala Ala Gly His Thr
            195                 200                 205

Phe Pro Asn Glu Thr Arg Arg Phe Trp Gln Gly His Arg Phe Leu Asn
            210                 215                 220

Phe Leu Leu Ala Cys Met Val Phe Ala Phe Val Ile Ser Trp Leu Phe
225                 230                 235                 240

His Phe Asn Val Pro Gly
                245
```

What is claimed is:

1. An isolated polynucleotide having a nucleotide sequence that encodes a zinc finger, C3HC4 type polypeptide having an amino acid sequence with at least 95 percent identity to the sequence set forth in SEQ ID NO:2.

\* \* \* \* \*